(12) United States Patent
Chang

(10) Patent No.: US 8,348,900 B2
(45) Date of Patent: Jan. 8, 2013

(54) SAFETY BOX FOR INTRAVENOUS INFUSION SET

(76) Inventor: Komas Chang, Taichung (TW)

( * ) Notice: Subject to any disclaimer, the term of this patent is extended or adjusted under 35 U.S.C. 154(b) by 48 days.

(21) Appl. No.: 13/008,198

(22) Filed: Jan. 18, 2011

(65) Prior Publication Data

US 2012/0181198 A1 Jul. 19, 2012

(51) Int. Cl.
*A61M 5/178* (2006.01)
(52) U.S. Cl. ............ 604/165.03; 604/177; 220/540
(58) Field of Classification Search ............ 604/165.03, 604/177; 220/540, DIG. 20
See application file for complete search history.

(56) References Cited

U.S. PATENT DOCUMENTS

| 5,921,969 A * | 7/1999 | Vallelunga et al. ............ 604/263 |
| 6,240,989 B1 * | 6/2001 | Masoud ........................ 150/149 |

\* cited by examiner

*Primary Examiner* — Kevin C Sirmons
*Assistant Examiner* — Deanna K Hall
(74) *Attorney, Agent, or Firm* — Rosenberg, Klein & Lee

(57) ABSTRACT

A safety box for use with an intravenous infusion set is disclosed to include a box body having a locating groove located on each of the front and rear sides thereof for receiving the flexible tube of the intravenous infusion set and a retaining hole located on one lateral side thereof, and a box cover hinged to the box body and having a hook block with two hooked portions selectively engageable into the retaining hole of the box body to temporarily or permanently lock the box cover to the box body.

3 Claims, 3 Drawing Sheets

SAFETY BOX FOR INTRAVENOUS INFUSION SET

BACKGROUND OF THE INVENTION

1. Field of the Invention

The present invention relates to medical implements and more particularly, to a safety box for intravenous infusion set.

2. Description of the Related Art

An intravenous infusion set, as shown in FIG. 1 (the safety box 100 excluded) generally includes a flexible tube 1, a needle 2 and a flexible wing plate 3 connected between the flexible tube 1 and the needle 2. During application, the needle 2 is inserted into the patient's vein, and then the flexible wing plate 3 is adhered to the body skin of the patient with a medical adhesive tape. After the infusion, the needle 2 is removed from the body of the patient, and capped with a protective cap 4 to avoid accidental injury or contamination. However, simply using the protective cap 4 to protect the used needle 2 cannot guarantee hundred percent safety. The protective cap 4 may be forced away from the needle 2 easily, causing an accidental injury. Further, after removal of the protective cap 4 from the needle 2 during the infusion, the user may forget to pick up the protective cap 4 for use after the service of the needle 2. After the infusion, the user may be unable to find out the protective cap 4 for capping on the used needle 2.

SUMMARY OF THE INVENTION

The present invention has been accomplished under the circumstances in view. It is one object of the present invention to provide a safety box, which is practical for use with an intravenous infusion set to prevent accidental contamination or injury after the service of the intravenous infusion set.

To achieve this and other objects of the present invention, a safety box comprises a box body comprising a locating groove located on each of the front and rear sides thereof for receiving the flexible tube of the intravenous infusion set and a retaining hole located on one lateral side thereof, and a box cover hinged to one lateral side of the box body opposite to the retaining hole and having a hook block for engaging into the retaining hole to lock the box cover in the close position. The hook block has a first hooked portion for engaging into the retaining hole to permanently lock the box cover to the box body in the close position, and a second hooked portion for engaging into the retaining hole to temporarily lock the box cover to the box body.

DETAILED DESCRIPTION OF THE PREFERRED EMBODIMENT

Figure 1:
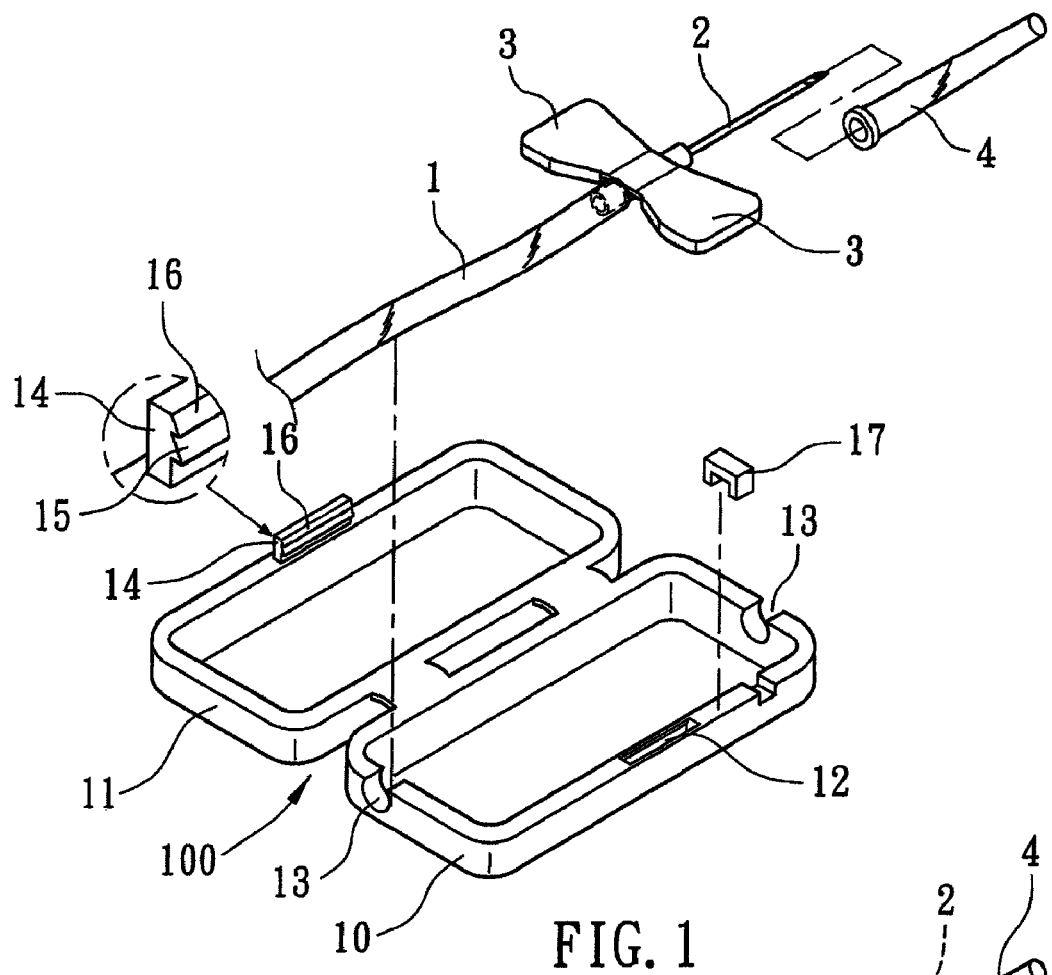
FIG. 1 is an opened view of a safety box for intravenous infusion set in accordance with the present invention.

Referring to FIGS. 1~5, a safety box 100 in accordance with the present invention is shown assembled with an intravenous infusion set comprising a flexible tube 1, a needle 2 and a flexible wing plate 3 connected between the flexible tube 1 and the needle 2.

The safety box 100 comprises a box body 10 and a box cover 11 hinged to one lateral side of the box body 10 and adapted for closing the box body 10. The box body 10 has a locating groove 13 located on each of the front and rear sides thereof for the passing of the flexible tube 1, and a retaining hole 12 located on the other lateral side thereof. The box cover 11 has a hook block 14 located on one lateral side thereof opposite to the other lateral side that is hinged to the box body 10. When the box cover 11 is closed on the box body 10, the hook block 14 is forced into engagement with the retaining hole 12 of the box body 10. The hook block 14 has a first hooked portion 15 and a second hooked portion 16. The second hooked portion 16 has a height relatively shorter than the first hooked portion 15. Further, a clamping plate 17 is clamped on the other lateral side of the box body 10 adjacent to the retaining hole 12.

Figure 2:
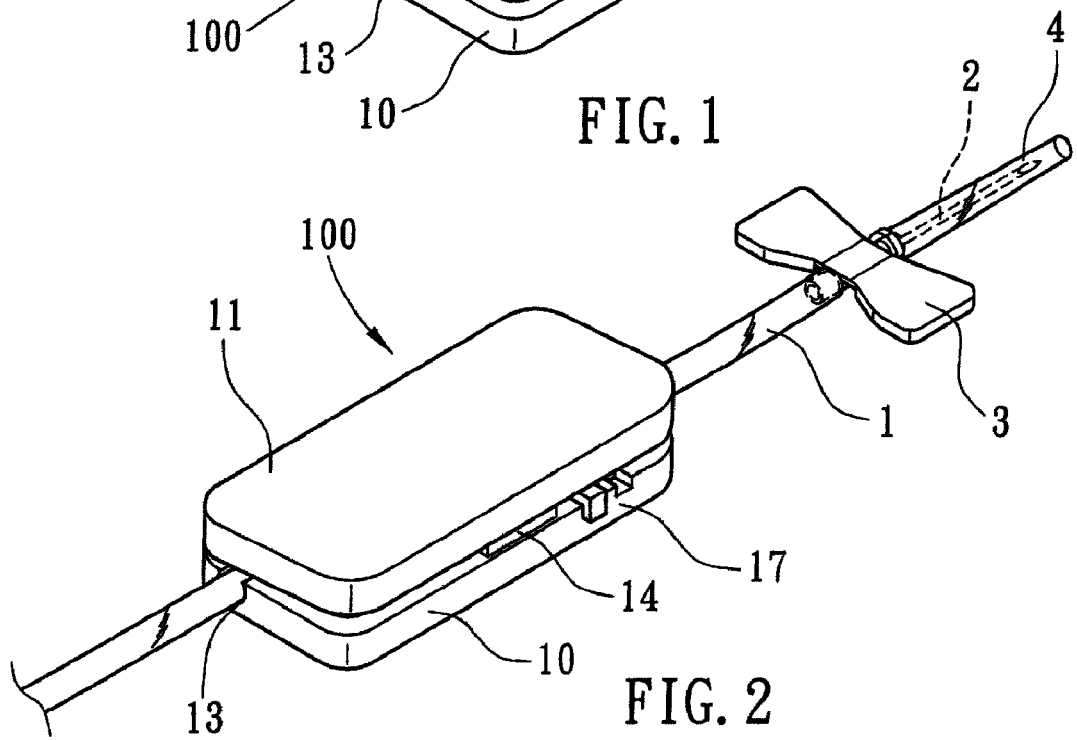
FIG. 2 is an elevational view of the present invention, illustrating the safety box assembled with the intravenous infusion set.
Figure 3:
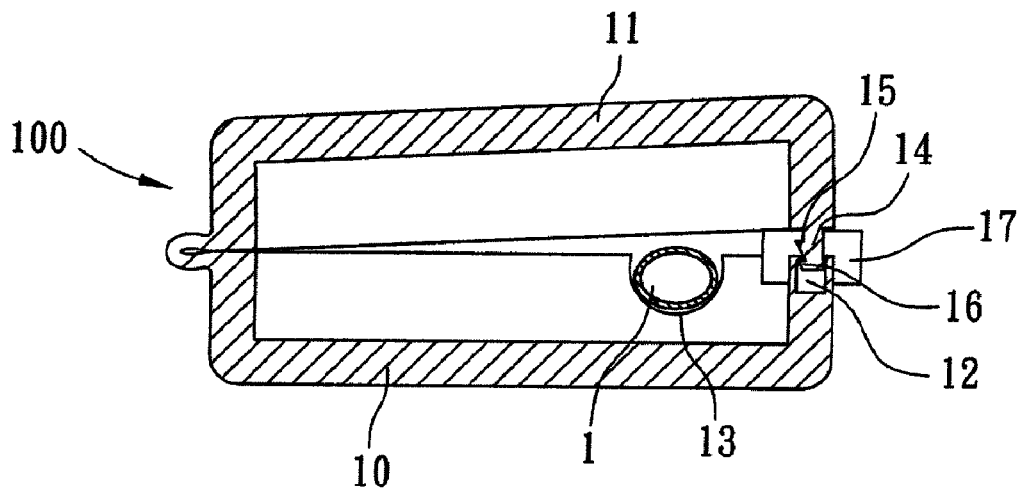
FIG. 3 is a sectional view of FIG. 2.
Figure 4:
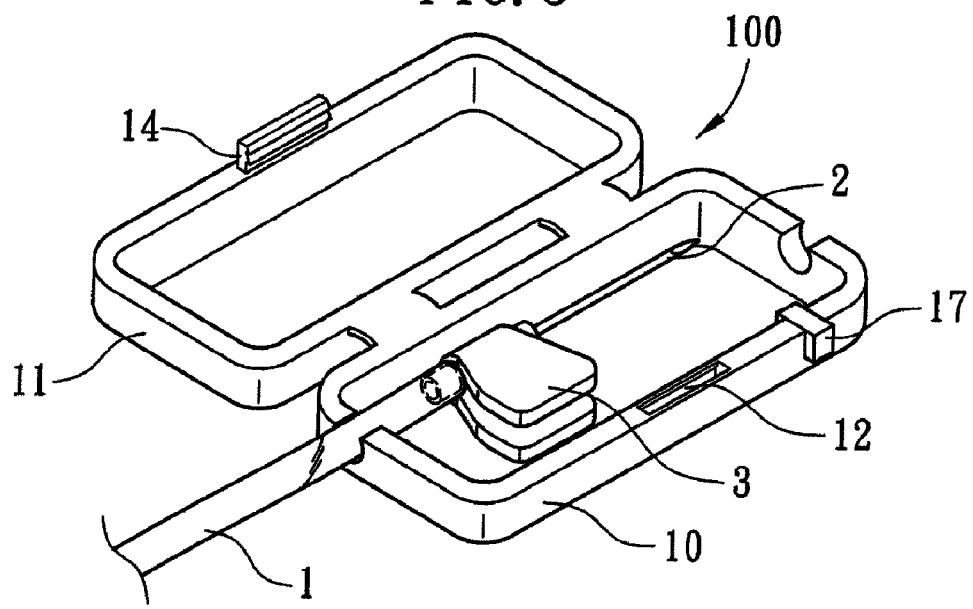
FIG. 4 is a schematic drawing of the present invention, illustrating the needle of the safety box opened and the intravenous infusion set received in the safety box.
Figure 5:
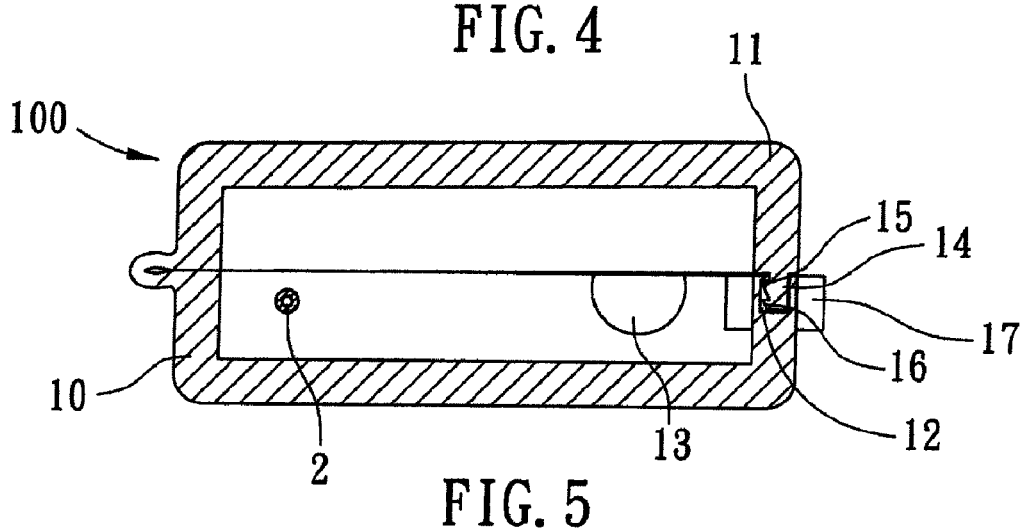
FIG. 5 is a sectional view of the safety box in accordance with the present invention.

The effects of the safety box 100 will be described hereinafter. As shown in FIGS. 2 and 3, before using the needle 2, the flexible tube 1 is set in the locating grooves 13 of the box body 10 and held down by the box cover 11. At this time, the clamping plate 17 works as a spacer sandwiched in between the box body 10 and the box cover 11, and the second hooked portion 16 of the hook block 14 is detachably forced into engagement with the retaining hole 12 of the box body 10. After the service of the needle 2, as shown in FIGS. 4 and 5, open the box cover 11 from the box body 10, and then receive the needle 2 and the flexible wing plate 3 in the box body 10, and then remove the clamping plate 17 from the box body 10, and then close the box cover 11 on the box body 10 to force the first hooked portion 15 and second hooked portion 16 of the hook block 14 into engagement with the retaining hole 12 of the box body 10. Thus, the safety box 100 is permanently closed to keep the used needle 2 on the inside, avoiding accidental contamination.

Figure 6:
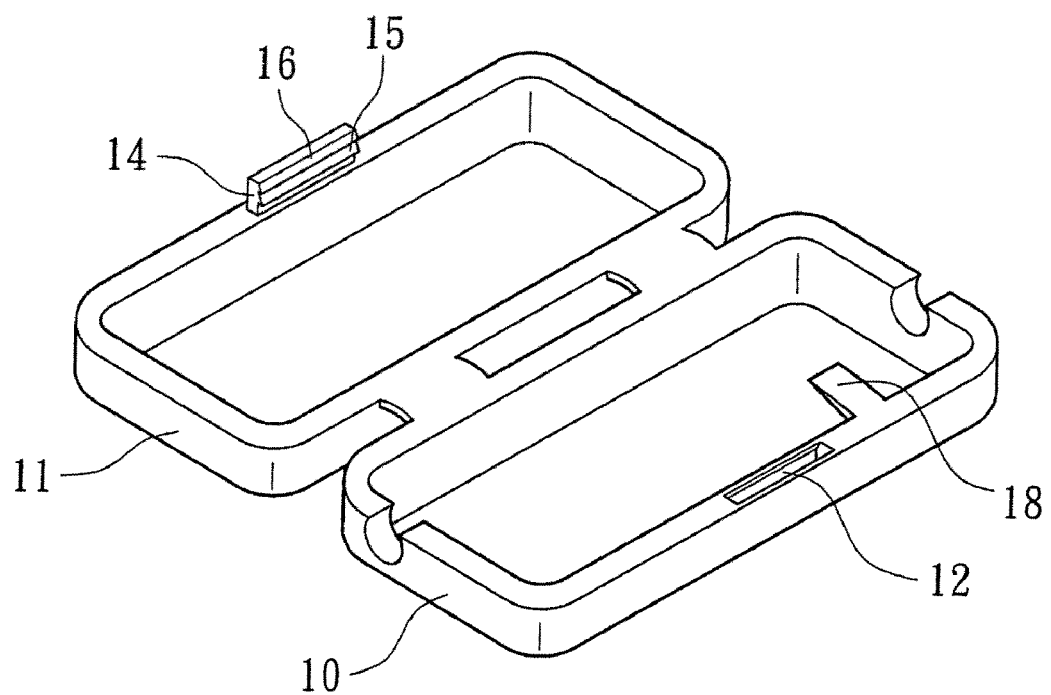
FIG. 6 is an opened view of an alternate form of the safety box in accordance with the present invention.
Figure 7:
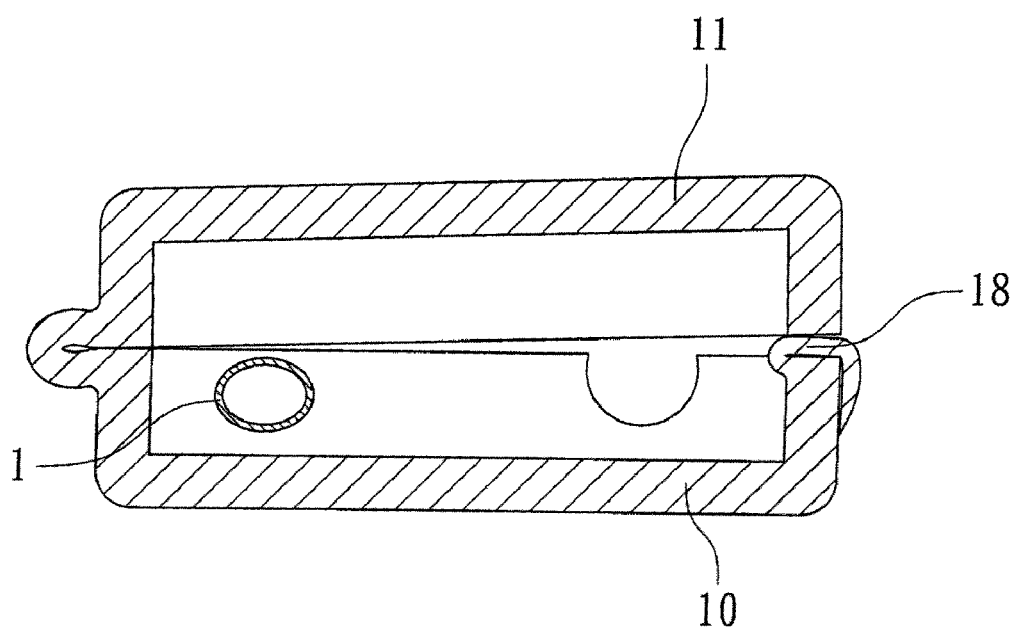
FIG. 7 is a sectional view of the safety box shown in FIG. 6.

FIGS. 6 and 7 show an alternate form of the present invention. This alternate form eliminates the aforesaid clamping plat 17, and the safety box 100 is substantially similar to the embodiment shown in FIGS. 1~5 with the exception that the safety box 100 of this alternate form further comprises a flexible protruding strip 18 formed integral with a part of the box body 10 (or the box cover 11) for setting in between the box body 10 and the box cover 11 (see FIG. 7) to prohibit engagement of the first hooked portion 15 of the hook block 14 into the retaining hole 12 of the box body 10. After the service of the needle 2 and setting of the used needle 2 and the flexible wing plate 3 in the box body 10, the flexible protruding strip 18 is released from the constraint and returned to its former shape, allowing the first hooked portion 15 and second hooked portion 16 of the hook block 14 to be forced into engagement with the retaining hole 12 of the box body 10. Thus, the safety box 100 is permanently closed to keep the used needle 2 on the inside, avoiding accidental contamination.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A safety box for use with an intravenous infusion set comprising a flexible tube, a needle and a flexible wing plate connected between said flexible tube and said needle, the safety box comprising:

a box body, said box body comprising opposing first lateral side and second lateral side, a front side, a rear side, a locating groove located on each of said front side and said rear side for receiving the flexible tube of said intravenous infusion set, and a retaining hole located on said second lateral side; and a box cover adapted for closing said box body to keep said needle in said box body after the service of said needle, said box cover comprising a first lateral side hinged to the first lateral side of said box body, a second lateral side opposite to the first lateral side of said box body, and a hook block located on the second lateral side for engaging into the retaining hole of said box body after closing of said box cover on said box body, said hook block comprising a first hooked portion for engaging into said retaining hole to permanently lock the second lateral side of said box cover to the second lateral side of said box body and a second hooked portion for engaging into said retaining hole to temporarily lock the second lateral side of said box cover to the second lateral side of said box body.

2. A safety box for use with an intravenous infusion set comprising a flexible tube, a needle and a flexible wing plate connected between said flexible tube and said needle, the safety box comprising:

a box body, said box body comprising opposing first lateral side and second lateral side, a front side, a rear side, a locating groove located on each of said front side and said rear side for receiving the flexible tube of said intravenous infusion set, and a retaining hole located on said second lateral side;

a box cover adapted for closing said box body to keep said needle in said box body after the service of said needle, said box cover comprising a first lateral side hinged to the first lateral side of said box body, a second lateral side opposite to the first lateral side of said box body, and a hook block located on the second lateral side for engaging into the retaining hole of said box body after closing of said box cover on said box body, said hook block comprising a first hooked portion for engaging into said retaining hole to permanently lock the second lateral side of said box cover to the second lateral side of said box body and a second hooked portion for engaging into said retaining hole to temporarily lock the second lateral side of said box cover to the second lateral side of said box body; and a clamping plate for clamping on the second lateral side of said box body to prohibit the first hooked portion of said hook block from being engaged into said retaining hole and to let the second hooked portion of said hook block be forced into engagement with said retaining hole.

3. A safety box for use with an intravenous infusion set comprising a flexible tube, a needle and a flexible wing plate connected between said flexible tube and said needle, the safety box comprising:

a box body, said box body comprising opposing first lateral side and second lateral side, a front side, a rear side, a locating groove located on each of said front side and said rear side for receiving the flexible tube of said intravenous infusion set, and a retaining hole located on said second lateral side;

a box cover adapted for closing said box body to keep said needle in said box body after the service of said needle, said box cover comprising a first lateral side hinged to the first lateral side of said box body, a second lateral side opposite to the first lateral side of said box body, and a hook block located on the second lateral side for engaging into the retaining hole of said box body after closing of said box cover on said box body, said hook block comprising a first hooked portion for engaging into said retaining hole to permanently lock the second lateral side of said box cover to the second lateral side of said box body and a second hooked portion for engaging into said retaining hole to temporarily lock the second lateral side of said box cover to the second lateral side of said box body; and a flexible protruding strip extended from one of said box body and said box cover for detachably setting in between the second lateral side of said box body and the second lateral side of said box cover to prohibit the first hooked portion of said hook block from been engaged into said retaining hole and to let the second hooked portion of said hook block be forced into engagement with said retaining hole.

* * * * *